US011219753B2

(12) United States Patent
Higgins et al.

(10) Patent No.: US 11,219,753 B2
(45) Date of Patent: Jan. 11, 2022

(54) INTRAVASCULAR PUMP WITH EXPANDABLE AND COLLAPSIBLE INLET REGION AND METHODS THEREOF

(71) Applicant: Cardiovascular Systems, Inc., St. Paul, MN (US)

(72) Inventors: Joseph P. Higgins, Minnetonka, MN (US); Matthew W. Tilstra, Rogers, MN (US); Benjamin D. Haselman, St. Paul, MN (US); Matthew D. Cambronne, North Oaks, MN (US); Tristan A. Van de Moortele, Minneapolis, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 0 days.

(21) Appl. No.: 16/524,592

(22) Filed: Jul. 29, 2019

(65) Prior Publication Data

US 2020/0030512 A1    Jan. 30, 2020

Related U.S. Application Data

(60) Provisional application No. 62/711,870, filed on Jul. 30, 2018.

(51) Int. Cl.
*A61M 60/135*    (2021.01)
*A61M 60/148*    (2021.01)
(Continued)

(52) U.S. Cl.
CPC ........ *A61M 60/135* (2021.01); *A61M 60/148* (2021.01); *A61M 60/205* (2021.01);
(Continued)

(58) Field of Classification Search
CPC .... A61M 1/125; A61M 1/1024; A61M 1/122; A61M 1/1008; A61M 1/1029; A61M 1/1086; A61M 60/81; A61M 60/861
(Continued)

(56) References Cited

U.S. PATENT DOCUMENTS

| 2011/0004046 A1 | 1/2011 | Campbell et al. |
| 2012/0172655 A1 * | 7/2012 | Campbell ............. A61M 25/04 |
| | | 600/16 |

(Continued)

FOREIGN PATENT DOCUMENTS

| JP | 2012-531975 | 12/2012 |
| JP | 2016-524937 | 8/2016 |

(Continued)

OTHER PUBLICATIONS

International Search Report and Written Opinion of the International Searching Authority, dated Oct. 7, 2019, for PCT Patent Application No. PCT/US19/044066, filed Jul. 30, 2019.
(Continued)

*Primary Examiner* — Michael W Kahelin
(74) *Attorney, Agent, or Firm* — Barnes & Thornburg LLP; Jeffrey R. Stone

(57) ABSTRACT

The present invention provides an intravascular blood pump comprising a housing region that may be expandable and collapsible, wherein the expandable housing region includes the inlet to the pump and wherein the distal diameter of the expandable housing region, including the inlet, is larger than a proximal diameter of the expandable housing region. A non-expandable region may be provided and disposed between the expandable housing region and the pump assembly of the intravascular blood pump.

34 Claims, 4 Drawing Sheets

(51) Int. Cl.
  *A61M 60/40* (2021.01)
  *A61M 60/50* (2021.01)
  *A61M 60/205* (2021.01)
  *A61M 60/857* (2021.01)
(52) U.S. Cl.
  CPC ............. *A61M 60/40* (2021.01); *A61M 60/50* (2021.01); *A61M 60/857* (2021.01)
(58) Field of Classification Search
  USPC .......................................................... 600/16
  See application file for complete search history.

(56) References Cited

U.S. PATENT DOCUMENTS

| | | | |
|---|---|---|---|
| 2012/0178986 A1* | 7/2012 | Campbell | A61M 1/101 600/16 |
| 2016/0129170 A1* | 5/2016 | Siess | A61M 1/101 600/18 |
| 2016/0136343 A1* | 5/2016 | Anagnostopoulos | A61M 1/1005 |
| 2016/0354525 A1 | 12/2016 | McBride et al. | |
| 2017/0049946 A1* | 2/2017 | Kapur | A61B 5/042 |
| 2019/0105437 A1* | 4/2019 | Siess | A61M 60/205 |

FOREIGN PATENT DOCUMENTS

| | | |
|---|---|---|
| WO | 2011/003043 | 1/2011 |
| WO | 2014/164292 | 10/2014 |
| WO | 2014/203078 | 12/2014 |
| WO | 2017/162618 | 9/2017 |

OTHER PUBLICATIONS

International Preliminary Report on Patentability, dated Feb. 11, 2021, in PCT Patent Application No. PCT/US19/044066, filed Jul. 30, 2019.

* cited by examiner

INTRAVASCULAR PUMP WITH EXPANDABLE AND COLLAPSIBLE INLET REGION AND METHODS THEREOF

CROSS-REFERENCE TO RELATED APPLICATIONS

This application claims priority to U.S. Provisional Patent Application No. 62/711,870, filed Jul. 30, 2018 and titled INTRAVASCULAR PUMP WITH EXPANDABLE REGION AND PROFILES FOR SAME, the contents of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The invention relates to an intravascular blood pump with an expandable and collapsible inlet region.

Description of the Related Art

With reference to FIG. 1, the human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. The use of temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Known temporary ventricle assist devices ("VAD"), including LVAD and RVAD (right ventricular assist) devices, whether with integrated motor or an external motor, generally comprise the following elements mounted within a housing, listed in order from the inflow end to the outflow end: an inflow aperture(s); a stationary inducer, also known as a flow straightener; a rotational impeller; and a stationary diffuser and/or outflow structure; and an outflow aperture(s) as shown in the exemplary prior art pump and/or impeller assembly cross sectional and cutaway view of FIG. 2.

In FIG. 2, the known device 2 is oriented with the inflow end (distal end) on the left side of the drawing and the outflow end (proximal) on the right side, so that the incoming blood flow in the ventricle enters the device housing through the inflow aperture(s) (not shown), flows through the defined by the surrounding housing 14, ultimately entering the impeller/pump assembly 4. There, the incoming blood encounters the stationary inducer 6 before being urged forward by the rotating impeller 8. The blood flow may then be modified by a stationary diffuser and exits into the aorta via the housing's outflow aperture(s) 10.

Known VAD or LVAD devices further comprise a delivery configuration and a functional or working configuration, with the delivery configuration having a lower profile or smaller diameter than the functional or working configuration to, inter alia, facilitate atraumatic delivery through a delivery sheath. Stated differently, through various means the housing of the VAD or LVAD, and/or the blades of the impeller, may expand to achieve the functional or working configuration and collapse to achieve the delivery configuration. However, known devices collapse and expand the impeller blades and/or the housing wherein the collapsible and expandable housing surrounds at least a portion of the impeller in order to enable moving between an expanded or working configuration and/or require an integrated motor proximate the impeller. See, e.g., U.S. Pat. Nos. 7,027,875; 7,927,068; and 8,992,163.

Known LVAD devices will typically comprise an angled housing to accommodate the aortic arch, the angle or bend generally in the range of 135 degrees.

LVAD devices with integrated motors within the housing must be small enough to allow atraumatic intravascular translation and positioning within the heart. Though various means are known to collapse portions of the device while within the catheter or delivery sheath, including the housing and/or the impeller or parts thereof such as the blades, the size of the collapsed device may be limited by the integrated motor.

In addition, the known LVAD devices comprise a delivery configuration wherein the housing and/or impeller, e.g., the blades on the impeller, may be reduced in diameter and, when delivered distally from the delivery catheter or sheath, the collapsed elements are enabled to expand. These devices are limited in several respects. First, the collapsing and expanding comprises at least a portion of the housing that is occupied by the impeller. Second, the inflow region of the housing, that is the region distal to the rotational impeller and the stationary inducer or flow straightener, comprises an area of opportunity to optimize blood flow through the cannula or housing. Known LVAD or VAD devices do not take advantage of this opportunity. Third, known LVAD or VAD devices comprise a stationary inducer or flow straightener encountered by blood upon entry into the pump which can contribute to, inter alia, thrombosis and/or hemolysis. Fourth, reducing crossing profile of the VAD or LVAD device is critical for reasons discussed herein, a design requirement made more difficult by the need to extend electric leads across or along the housing of the device, wherein the electrical leads may be used for, e.g., powering and/or communicating with a motor or sensor(s) or other operational powered element. In this connection, electric leads require profile reduction to keep the crossing profile as low as possible, as well as insulation and/or spacing between adjacent leads where such insulation and/or spacing is necessary or desired.

Various embodiments of the present invention address these, inter alia, issues.

The figures and the detailed description which follow more particularly exemplify these and other embodiments of the invention.

DETAILED DESCRIPTION OF THE INVENTION

Generally, various embodiments of the present invention are directed to mechanical assist devices for pumping blood in a patient. Improved temporary LVAD or VAD blood pumps are described herein that are delivered percutaneously and intravascularly.

Figure 1:
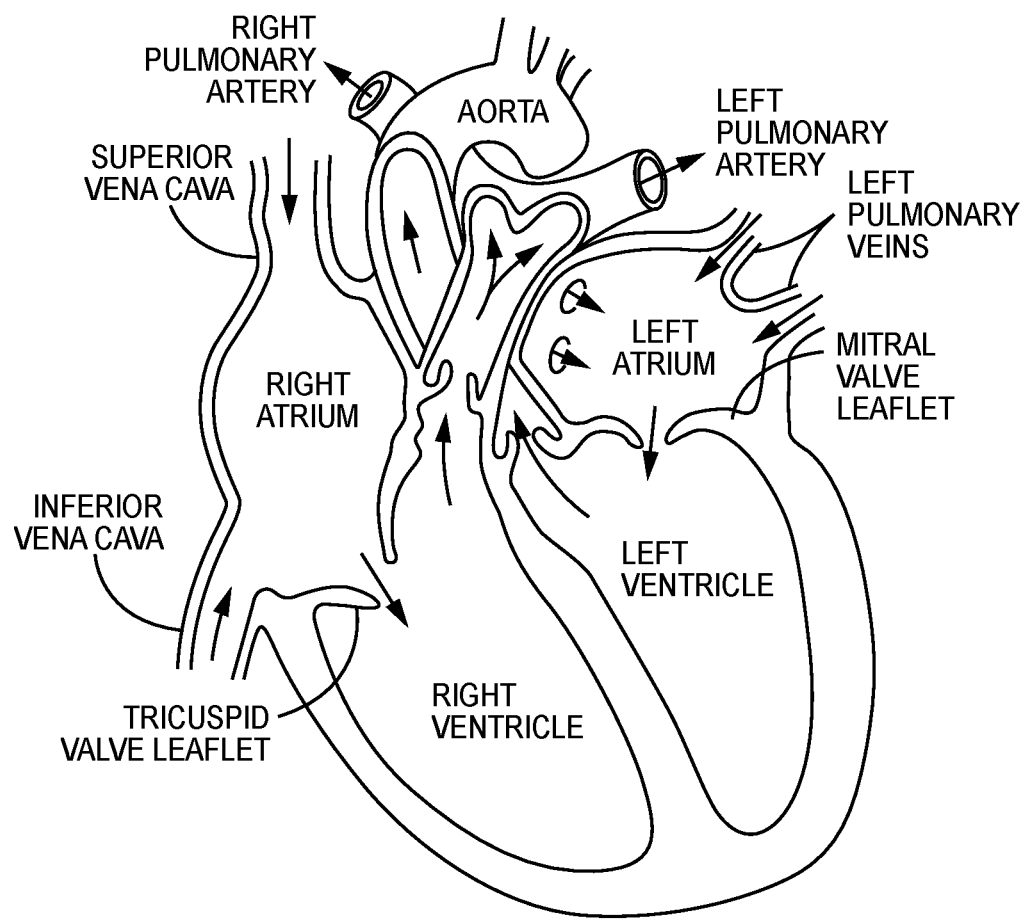
FIG. 1 is a cutaway view of the human heart.
Figure 2:
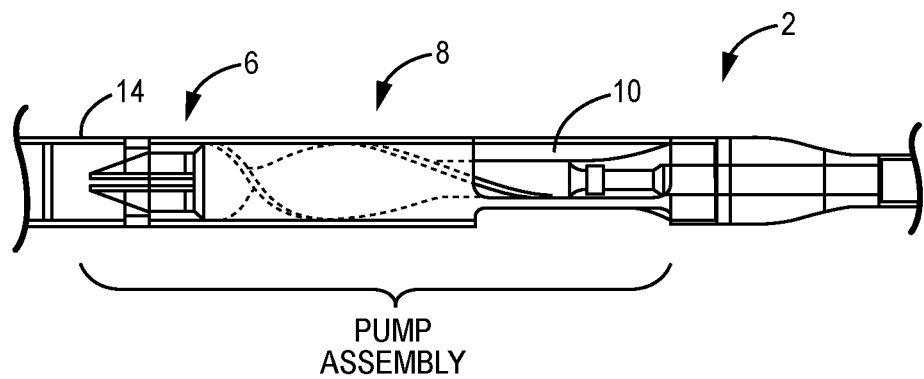
FIG. 2 is a cross-sectional view of a prior art device.
Figure 3:
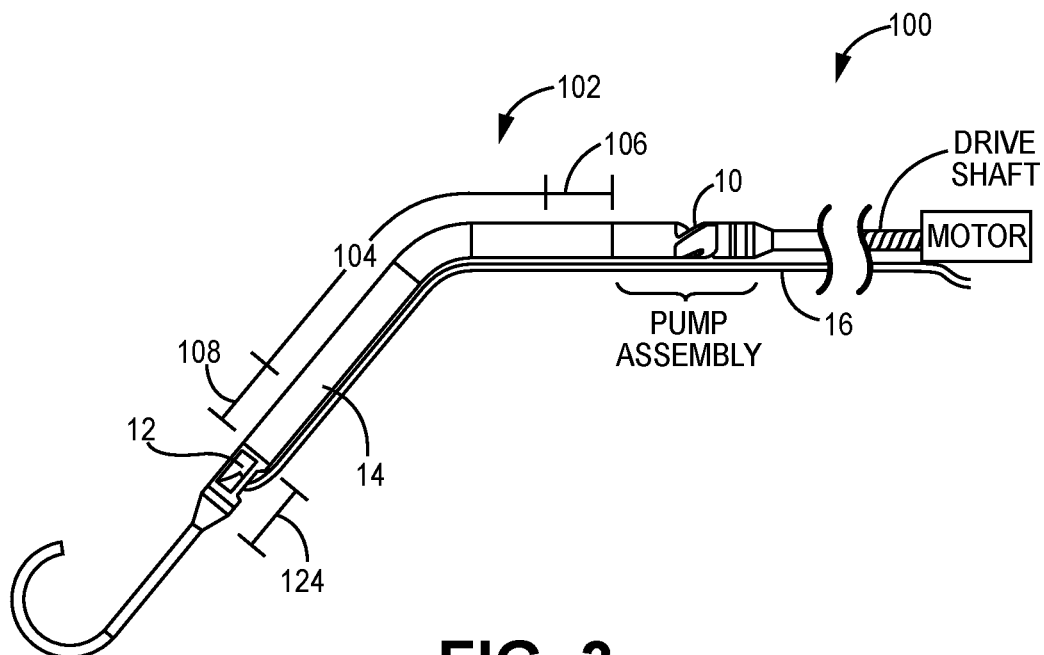
FIG. 3 is a side cutaway view of one embodiment of the present invention.

Referring now to FIG. 3, an exemplary LVAD blood pump 100 is illustrated, with inflow apertures 12 on the left side of the illustration and outflow apertures 10 on the right side of the device. The motor is shown as located on the proximal end of the device outside the patient's body and connected with a rotational drive shaft that is, in turn, connected with the impeller or rotor 8 or pump assembly. However, as is well known in the art, the motor may be located within the housing of the device itself, wherein the motor is typically mounted on the proximal side of the rotor 8 or impeller or pump assembly. Either of these configurations may be used together with various embodiments of the present invention as described herein.

The entire length of outer housing 14 is shown as comprising a relatively constant diameter from the inlet or inflow apertures 12 to the outlet or outflow apertures 10. Guide wire 16 is positioned alongside the exterior of the device until reaching the inlet apertures 12 where it enters the lumen of cannula C and extends distally therefrom as shown. Thus, the guide wire 16 does not pass through the impeller or rotor 8 or pump assembly. The configuration shown in FIG. 3 may comprise a delivery configuration with an expandable region 102 compressed within an introducer or delivery sheath or catheter 200.

With reference generally to the Figures, device 100 may comprise an expandable region 102 that may be located distal to the impeller or rotor or pump assembly, such that the housing diameter surrounding the impeller or rotor or pump assembly does not change diameter during delivery or during rotation. Stated differently, a proximal non-expandable region 122 may be provided and comprises at least the impeller or rotor or pump assembly and the housing surrounding that assembly does not expand or contract appreciably but may be flexible. Further, a distal non-expandable region 124 may also be provided comprising at least the inlet region including at least the inlet apertures 12. Thus, the expandable region 102 comprises a proximal end and a distal end. The proximal end of the expandable region 102 abuts or is adjacent to a distal end of the proximal non-expandable region 122 while the distal end of the expandable region 102 abuts or is adjacent to a proximal end of the distal non-expandable region 124. The housing H surrounding the non-expandable region(s) 122, 124 may, however, be flexible or pliable, but they are not disposed to a biased expansion.

Alternatively, the housing H of device 100 in FIG. 3 may be non-expandable.

Figure 4:
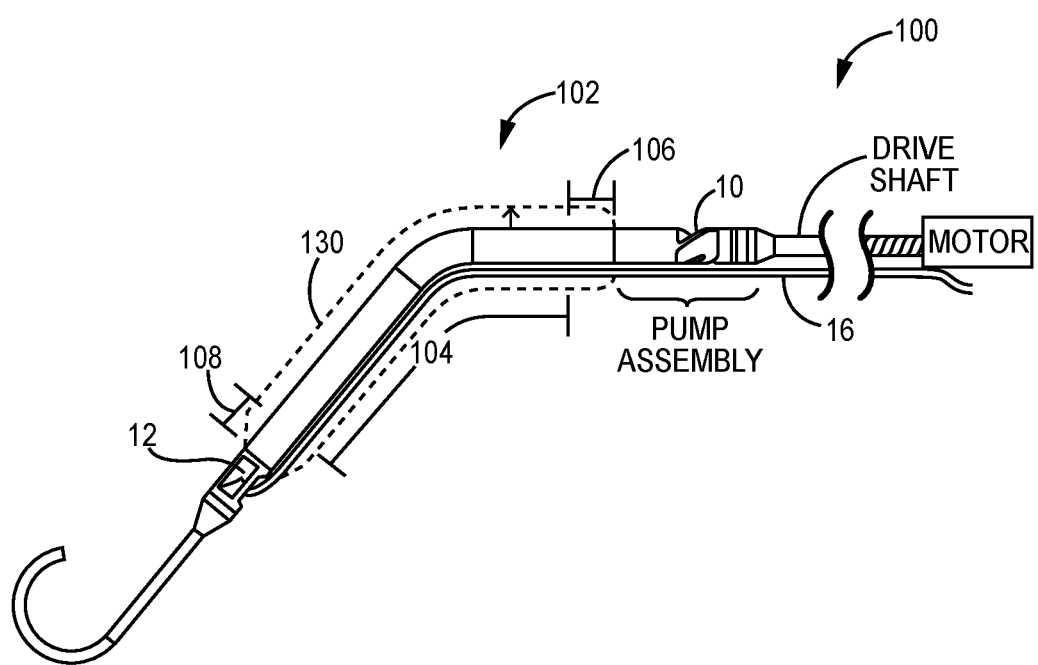
FIG. 4 is a side cutaway view of one embodiment of the present invention.

FIG. 4 illustrates an expandable embodiment of device 100 and in dashed lines the change in diameter to/from a collapsed, deformed expandable region to an exemplary expanded undeformed expandable region, extending distally from a point distal to the end of the impeller, rotor and/or pump assembly along the hollow cannula to a point just proximal of the inlet apertures. The expandable region 102 may expand to a maximum undeformed diameter within the range of 12-20 Fr, more preferably between 16-20 Fr. In contrast, the unexpanded region remains at a substantially fixed diameter within the range of 9 to 12 Fr.

With continued reference to FIGS. 3 and 4, and the remaining Figures generally, the device 100 may comprise an expandable region 102 that may be, either partially or completely, biased to the expanded configuration and, therefore, comprise a material or structure that facilitates expansion and may be biased to expand. Exemplary construction of the expandable region 102 may comprise a support structure 130 that is surrounded by an outer material, e.g., a jacket or coating or sleeve comprised of a plastic or polymeric material that accommodates an expansion of the underlying support structure as is known in the art. The support structure 130 may be formed of a shape memory material, for example Nitinol or similar. Other materials may comprise gold, tantalum, stainless steel, metal alloys, aerospace alloys and/or polymers including polymers that expand and contract upon exposure to relative heat and cold. In other cases, at least a portion of the expandable region 102, e.g., a central expandable section 104 discussed infra, may comprise a polymeric or other material sleeve that is configured to allow and/or accommodate expansion and collapsing and a support structure 130 may be omitted. FIG. 4 provides a rotational drive shaft connected with the impeller assembly and is, in turn, connected with a prime mover such as an electric motor that is located outside the patient's body. It will be understood, however, that the various embodiments of the inventions discussed herein may also be used in combination with blood pumps comprising motors integrated therein, i.e., no external motor. Further, as discussed above, device 100 may comprise an expandable housing H or region 102 or may be non-expandable.

FIGS. 3 and 4 each illustrate a proximal end 106 and a distal end 108 of expandable region 102. As shown, the proximal end 106 may taper or decrease in expanded inner and outer diameter moving in the proximal direction, and distal end 108 may taper or decrease in expanded inner and outer diameter moving in the distal direction.

In many of the embodiments described herein, the expandable region 102 may comprise a single expandable region, without need or reason to distinguish between a proximal transition section, central expandable section and/or distal transition section.

Generally, the expandable region 102 of the present invention may comprise a support structure 130 surrounded by a polymer coating or jacket that adapts to expansion and collapsing of the expandable region 102.

Further, the support structure 130 may comprise an expandable stent-like structure formed of a series of cells formed from interacting and/or interconnected wires and/or struts and that enable collapsing and biased expansion of a structure, e.g., a stent, as is known in the art. For example, see U.S. Pat. No. 5,776,183 to Kanesaka; U.S. Pat. No. 5,019,090 to Pinchuk; U.S. Pat. No. 5,161,547 to Tower; U.S. Pat. No. 4,950,227 to Savin; U.S. Pat. No. 5,314,472 to Fontaine; U.S. Pat. Nos. 4,886,062 and 4,969,458 to Wiktor; and U.S. Pat. No. 4,856,516 to Hillstead, the disclosures of each of which are hereby incorporated in their entirety by reference.

The expandable region 102 described herein is merely exemplary and not limiting in any regard. As such, any expandable housing H of a blood pump device 100 is readily adaptable to the various embodiments of the present invention relating to insulation and/or spacing and/or profile reduction or integration of electrical leads or conductors E within or along the blood pump housing. Expandable region 102 may also comprise a single region capable of expansion and collapse.

Figure 5:
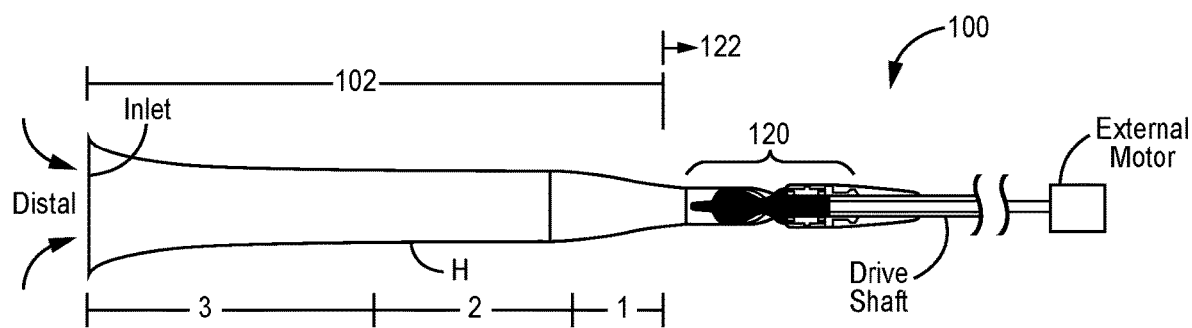
FIG. 5 is a side cutaway view of one embodiment of the present invention.

Turning now to FIG. 5, the expandable region 102 is disposed at a point distal to pump assembly 122 and comprises a lumen therethrough. The expandable region 102 may comprise three Regions 1, 2, 3. Region 1 comprises a section of a cone with a smaller diameter at the proximal end and a larger diameter at the distal end which may also form or define the base of the cone section. Region 2, disposed distal to Region 1, comprises a generally cylindrical profile shape with a diameter that is substantially the same as the diameter of the base of the cone of Region 1. Alternatively, Region 2 may comprise a diameter at its proximal end that matches the diameter of the base of the cone of Region 1, then slowly increasing diameter moving from proximal to distal through Region 2. Region 3 is disposed distal to Region 2 and comprises an increasing diameter to a maximum diameter at its distal end which is also the inlet for device 100. As shown, a flared or bell-shaped distal end or inlet defines the distal end of Region 3, however a non-flared conical shape may also be employed for Region 3 and its distal end. Also as shown, a non-expandable region 122 may be disposed proximal to the distal end of expandable region 102 and non-expandable region 122 may be disposed between impeller assembly 120 and expandable region 102. Regions 1, 2 and 3 may also be referred to herein as first Region, second Region and third Region, respectively.

Figure 6:
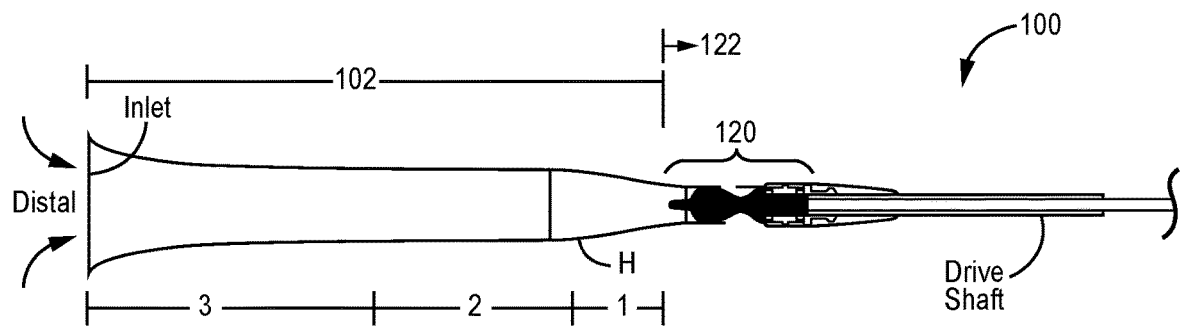
FIG. 6 is a side cutaway view of one embodiment of the present invention.

FIG. 6 is similar to FIG. 5, but a smaller version in terms of diameter than FIG. 5's expandable region 102.

Figure 7:
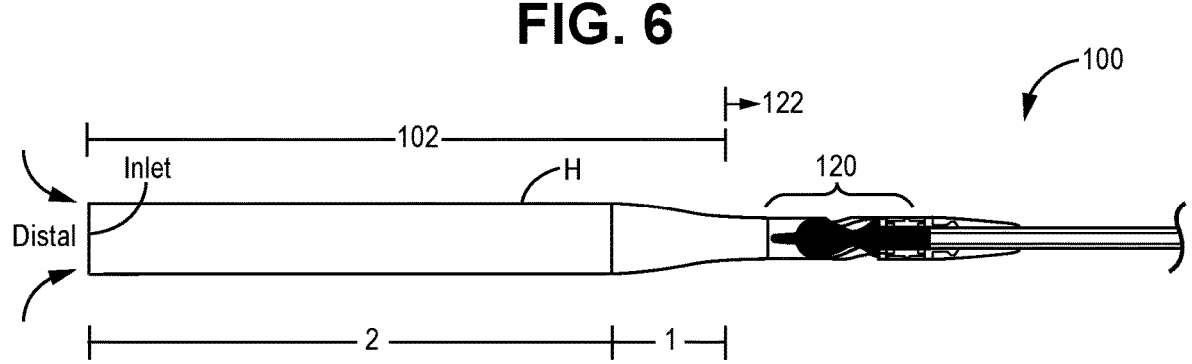
FIG. 7 is a side cutaway view of one embodiment of the present invention.

FIG. 7 comprises an expandable region 102 comprising two Regions, Region 1 which is similar to that of FIGS. 4 and 5. Region 2 is positioned distal to Region 1 and comprises a constant diameter along its length to the inlet defined at the distal end of Region 2. The diameter of Region 2 is substantially the same as the diameter of the distal end of Region 1, i.e., the base of the cone of Region 1 which is smaller than the diameter of its proximal end. Accordingly, The diameter of the distal end of expandable region 102 is larger than the diameter of the distal end of expandable region 102. As with FIGS. 5 and 6, a non-expandable region 122 may be disposed proximal to the distal end of expandable region 102 and non-expandable region 122 may be disposed between impeller assembly 120 and expandable region 102.

Figure 8:
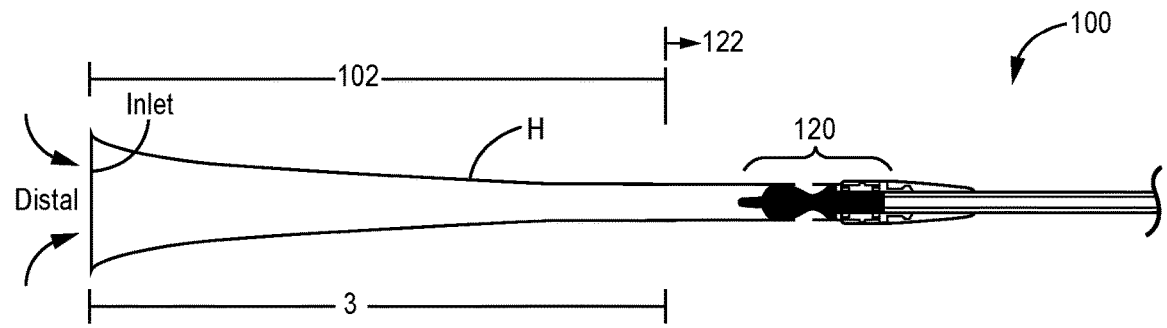
FIG. 8 is a side cutaway view of one embodiment of the present invention.

FIG. 8 provides an expandable region 102 with a single Region. Thus, Region 3 provides a slowly increasing diameter moving from proximal to distal away from non-expandable region 122 to the outlet at the distal end of the expandable region 102. As shown, the diameter of Region 3 increases at an increasing rate moving from proximal to distal to form a bell-shape or a flared profile. Alternatively, as with FIGS. 5-7, Region 3 in FIG. 8 may comprise a conical profile. Finally, as a non-expandable region 122 may be disposed proximal to the distal end of expandable region 102 and non-expandable region 122 may be disposed between impeller assembly 120 and expandable region 102.

The expandable region 102 in all illustrated cases may also collapse with expansion to the illustrated working configuration as described supra.

Thus, the inner diameter of the expanded expandable region 102 provides a lumen defined by the expanded expandable region 102. Thus, expandable region 102 comprises, at its distal end, an increased inner diameter and area compared with the inner diameter and area of the lumen defined by the expanded expandable region 102 at its proximal end as well as the inner diameter and area of the non-expandable region 122 and impeller assembly 120. As a result, fluid flow is optimized through the lumen of the expandable region 102, through non-expandable region 122 and impeller assembly 120, and ultimately, through outlet apertures. Moreover, the outer diameter of the distal end of the expanded expandable region 102 is larger than the outer diameter of the proximal end of the expanded expandable region 102 as well as the outer diameter of the non-expandable region 122 as shown in the Figures. Expandable region 102, non-expandable region 122 and impeller assembly 120 are shown as operatively connected and in fluid communication with each other so that fluid drawn into the inlet is moved through the lumen of the expandable region 102, through the lumen of the no-expandable region 122 and into the impeller assembly 120.

The description of the invention and is as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A blood pump comprising:
a non-expandable impeller assembly comprising an inner diameter;
a collapsible and expandable region disposed distal to, and in fluid communication with, the non-expandable impeller assembly and comprising:
a collapsible and expandable housing defining a lumen therethrough, and defining a proximal end with an outer diameter and an inner diameter, and
a distal end with an outer diameter and an inner diameter; and
a non-expandable inlet region defining a plurality of inlet apertures between a proximal end and a distal end of the non-expandable inlet region, the plurality of inlet apertures in fluid communication with, and disposed distally to, the collapsible and expandable region,
wherein the collapsible and expandable region is adapted to expand to an expanded configuration wherein the inner diameter of the distal end of the collapsible and expandable region is greater than the inner diameter of the proximal end of the collapsible and expandable region.

2. The blood pump of claim 1, wherein the outer diameter of the distal end of the collapsible and expandable region is greater than the outer diameter of the proximal end of the collapsible and expandable region.

3. The blood pump of claim 1, wherein the collapsible and expandable region comprises a single region having an inner diameter that decreases from the distal end of the collapsible and expandable region to the proximal end of the collapsible and expandable region.

4. The blood pump of claim 3, wherein the inner diameter of the non-expandable impeller assembly is the same as the inner diameter of the proximal end of the collapsible and expandable region.

5. The blood pump of claim 1, further comprising the distal end of the collapsible and expandable region comprising a flared profile.

6. The blood pump of claim 1, wherein the collapsible and expandable region comprises a shape memory material.

7. The blood pump of claim 6, wherein the shape memory material comprises a metal and/or a polymer.

8. The blood pump of claim 1, wherein the collapsible and expandable region is biased to expand.

9. The blood pump of claim 1, wherein at least a portion of the collapsible and expandable region comprises at least one of the outer profile shapes of the group consisting of: cylindrical, elliptical, conical, flared, and bell-shaped.

10. The blood pump of claim 1, wherein the collapsible and expandable region comprises a support structure comprising at least one of a stent structure and a polymer.

11. The blood pump of claim 1, wherein the collapsible and expandable region comprises an expandable stent having at least one stent cell pattern.

12. The blood pump of claim 11, wherein the expandable stent comprises at least one second stent cell pattern that is different from the first stent cell pattern.

13. A blood pump comprising:
A non-expandable impeller assembly, comprising an inner diameter;
a collapsible and expandable region disposed distal to, and in fluid communication with, the non-expandable impeller assembly and comprising
a collapsible and expandable housing defining a lumen therethrough, and defining a proximal end with an outer diameter and an inner diameter,
a distal end with an outer diameter and an inner diameter,
a first region comprising a decreasing inner diameter moving in the proximal direction, the first region disposed distal to, and in fluid communication with, the non-expandable impeller assembly, and
a second region of constant inner diameter, the second region disposed proximal to and in fluid communication with, the first region, and
wherein the collapsible and expandable region is adapted to expand to an expanded configuration wherein the inner diameter of the distal end of the collapsible and expandable region is greater than the inner diameter of the proximal end of the collapsible and expandable region; and
a non-expandable inlet region defining a plurality of inlet apertures between a proximal end and a distal end of the non-expandable inlet region, the plurality of inlet apertures in fluid communication with, and disposed distally to, the collapsible and expandable region.

14. The blood pump of claim 13, wherein the collapsible and expandable region comprises a shape memory material.

15. The blood pump of claim 14, wherein the shape memory material comprises a metal and/or a polymer.

16. The blood pump of claim 13, wherein the collapsible and expandable region is biased to expand.

17. The blood pump of claim 13, wherein at least a portion of the collapsible and expandable region comprises at least one of the outer profile shapes of the group consisting of: cylindrical, elliptical, conical, flared, and bell-shaped.

18. The blood pump of claim 13, wherein the collapsible and expandable region comprises a support structure comprising at least one of a stent structure and a polymer.

19. The blood pump of claim 13, wherein the collapsible and expandable region comprises an expandable stent having at least one stent cell pattern.

20. The blood pump of claim 19, wherein the expandable stent comprises at least one second stent cell pattern that is different from the first stent cell pattern.

21. A blood pump comprising:
A non-expandable impeller assembly; and
a collapsible and expandable region disposed distal to, and in fluid communication with, the non-expandable impeller assembly and comprising
a collapsible and expandable housing defining a lumen therethrough, and defining a proximal end with an outer diameter and an inner diameter,
a distal end with an outer diameter and an inner diameter,
a first region comprising a decreasing inner diameter moving in the proximal direction, the first region disposed distal to, and in fluid communication with, the non-expandable impeller assembly,
a second region of constant inner diameter, the second region disposed distal to and in fluid communication with, the first region, and a third region of decreasing inner diameter moving in the proximal direction, the third region disposed distal to, and in fluid communication with, the second region, a distal-most end of the third region comprising a distal-most end of the collapsible and expandable region, wherein the collapsible and expandable region is adapted to expand to an expanded configuration wherein the inner diameter of the distal-most end of the third region of the collapsible and expandable region defines the greatest inner diameter of the collapsible and expandable region, and wherein the collapsible and expandable region defines an inlet, the inlet defined by the distal-most end of the collapsible and expandable region.

22. The blood pump of claim 21, further comprising the distal end of the collapsible and expandable region comprising a flared profile.

23. The blood pump of claim 21, wherein the collapsible and expandable region comprises a shape memory material.

24. The blood pump of claim 23, wherein the shape memory material comprises a metal and/or a polymer.

25. The blood pump of claim 21, wherein the collapsible and expandable region is biased to expand.

26. The blood pump of claim 21, wherein at least a portion of the collapsible and expandable region comprises at least one of the outer profile shapes of the group consisting of: cylindrical, elliptical, conical, flared, and bell-shaped.

27. The blood pump of claim 21, wherein the collapsible and expandable region comprises a support structure comprising at least one of a stent structure and a polymer.

28. The blood pump of claim 21, wherein the collapsible and expandable region comprises an expandable stent having at least one stent cell pattern.

29. The blood pump of claim 28, wherein the expandable stent comprises at least one second stent cell pattern that is different from the first stent cell pattern.

30. The blood pump of claim 21, further comprising a non-expandable inlet region defining a plurality of inlet apertures between a proximal end and a distal end of the non-expandable inlet region, the plurality of inlet apertures in fluid communication with, and disposed distally to, the third region of the collapsible and expandable region.

31. The blood pump of claim 21, further comprising a non-expandable region positioned distal to the non-expandable impeller assembly and proximal to the first region of the collapsible and expandable region, the non-expandable region in fluid communication with the non-expandable impeller assembly and the first region of the collapsible and expandable region.

32. The blood pump of claim 21, wherein the inner diameter of the non-expandable impeller assembly is the same as the inner diameter of the proximal end of the first region of the collapsible and expandable region.

33. The blood pump of claim 21, wherein the outer diameter of the distal end of the third region of the collapsible and expandable region is greater than the outer diameter of the proximal end of the first region of the collapsible and expandable region.

34. The blood pump of claim 21, wherein the inlet comprises at least one aperture.

* * * * *